(12) United States Patent
Nishigaki et al.

(10) Patent No.: US 7,699,777 B2
(45) Date of Patent: Apr. 20, 2010

(54) ULTRASONIC DIAGNOSTIC APPARATUS

(75) Inventors: Morio Nishigaki, Kanagawa (JP); Hiroshi Fukukita, Tokyo (JP)

(73) Assignee: Panasonic Corporation, Osaka (JP)

( * ) Notice: Subject to any disclaimer, the term of this patent is extended or adjusted under 35 U.S.C. 154(b) by 805 days.

(21) Appl. No.: 10/583,025

(22) PCT Filed: Jul. 25, 2005

(86) PCT No.: PCT/JP2005/013586

§ 371 (c)(1),
(2), (4) Date: Jun. 15, 2006

(87) PCT Pub. No.: WO2006/022106

PCT Pub. Date: Mar. 2, 2006

(65) Prior Publication Data

US 2007/0160540 A1    Jul. 12, 2007

(30) Foreign Application Priority Data

Aug. 24, 2004    (JP) .............................. 2004-244117

(51) Int. Cl.
*A61B 8/00* (2006.01)
(52) U.S. Cl. .......................... 600/437; 600/407; 363/59; 363/62; 363/60; 363/61; 327/536; 327/537; 327/538; 320/166
(58) Field of Classification Search ................. 600/437, 600/407; 327/518, 536–538; 216/6; 361/2, 361/3, 5, 6, 7, 18; 363/59–62; 320/166
See application file for complete search history.

(56) References Cited

U.S. PATENT DOCUMENTS 3,681,977 A * 8/1972 Wendt et al. ................. 600/451

(Continued)

FOREIGN PATENT DOCUMENTS

JP    3-085146    4/1991

(Continued)

OTHER PUBLICATIONS

International Search Report, mailed Aug. 23, 2005.

*Primary Examiner*—Eric F Winakur
*Assistant Examiner*—Joel F Brutus
(74) *Attorney, Agent, or Firm*—Hamre, Schumann, Mueller & Larson, P.C.

(57) ABSTRACT

There are provided transducers, transmission pulse generators for transmitting pulses to the transducers, a transmission power source for supplying power to the transmission pulse generators, and an output side capacitor 7 for stabilizing a voltage of the transmission power source. The transmission power source includes a plurality of mode-specific power sources 1A and 1B for outputting a constant voltage, and a mode changeover switch 6 provided between the mode-specific power sources and the output side capacitor. The transmission power source further includes a power supplying power source 2 connected to the mode-specific power sources for supplying power, and a power regeneration capacitor 4 with a larger capacity than that of the output side capacitor, one electrode terminal of which is connected to a connection point between the power supplying power source and the mode-specific power sources and the mode changeover switch, and the other electrode terminal of which is connected to ground. The mode changeover switch is capable of connecting the power regeneration capacitor, instead of each of the mode-specific power sources, to the output side capacitor. There is provided an ultrasonic diagnostic apparatus that reuses power stored in the output side capacitor to reduce power consumption.

8 Claims, 5 Drawing Sheets

U.S. PATENT DOCUMENTS

| | | | |
|---|---|---|---|
| 4,218,768 A * | 8/1980 | Hassler | 367/105 |
| 4,451,909 A * | 5/1984 | Kodera et al. | 367/99 |
| 2002/0057540 A1* | 5/2002 | Ito et al. | 361/18 |
| 2004/0008094 A1* | 1/2004 | Niemi | 333/101 |

FOREIGN PATENT DOCUMENTS

| | | |
|---|---|---|
| JP | 11-290321 | 10/1999 |
| JP | 2001-292567 | 10/2001 |
| JP | 2002-369405 | 12/2002 |
| JP | 2004-159812 | 6/2004 |

* cited by examiner

ULTRASONIC DIAGNOSTIC APPARATUS

TECHNICAL FIELD

The present invention relates to an ultrasonic diagnostic apparatus for transmitting and receiving an ultrasonic wave with ultrasonic transducers to obtain information about the interior of the body, and particularly to a circuit for driving the transducers.

BACKGROUND ART

The following principle of ultrasonic diagnostic apparatuses already has been well known: an ultrasonic wave is transmitted to the inside of the body and a reflected wave thereof is received by using a transducer array, whereby two-dimensional information about the interior of the body is obtained.

Figure 4:
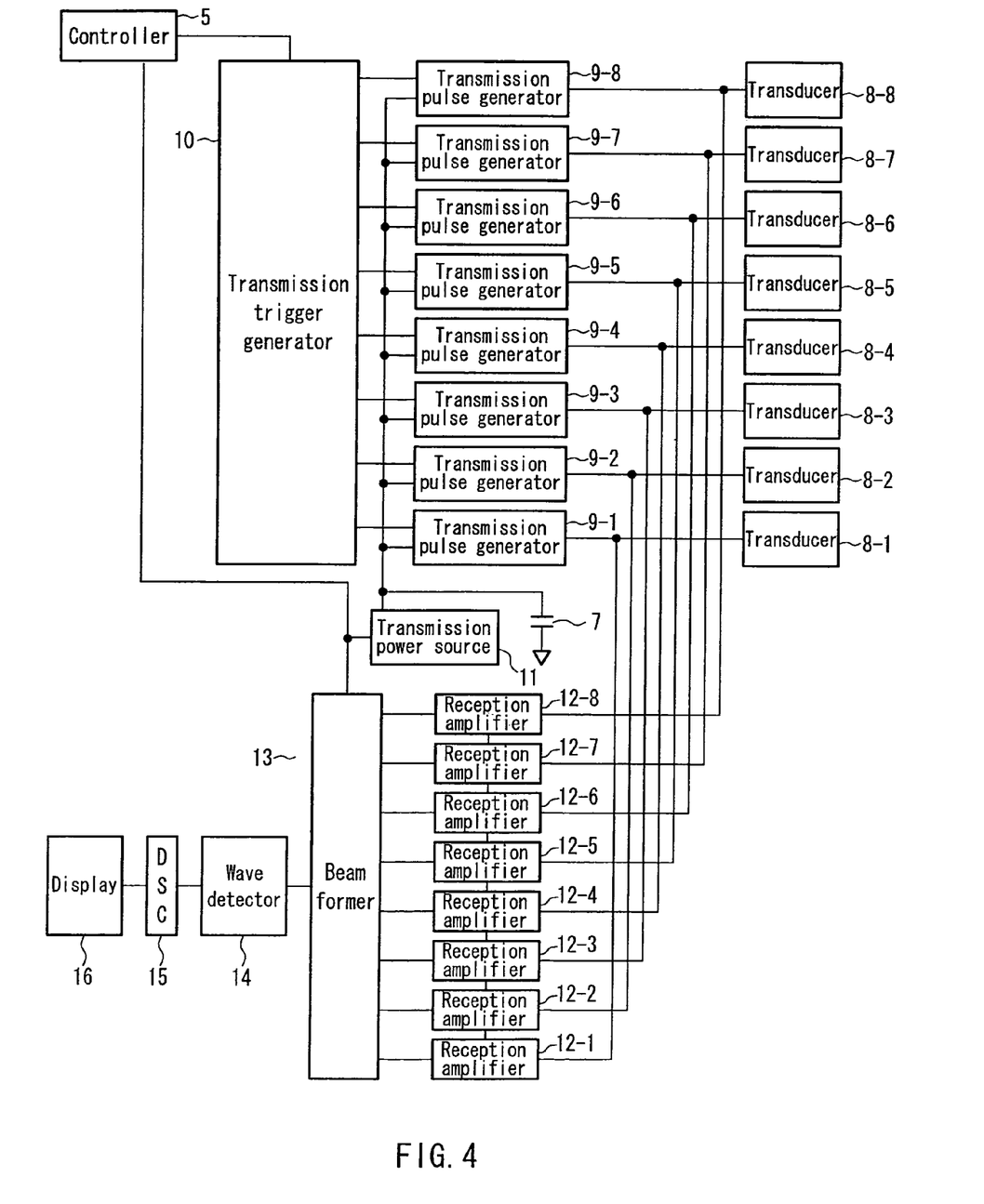
FIG. 4 is a block diagram of a conventional sector scanning type ultrasonic diagnostic apparatus.

An ultrasonic diagnostic apparatus that performs sector scanning by using a transducer array is configured as shown in FIG. 4, for example. An operation of the ultrasonic diagnostic apparatus that performs sector scanning will be described with reference to FIG. 4. Transducers 8-1 to 8-8 for transmitting and receiving an ultrasonic wave are connected with transmission pulse generators 9-1 to 9-8, respectively, for generating transmission pulses for driving the transducers 8-1 to 8-8. A transmission trigger generator 10 generates trigger pulses that allow the transmission pulse generators 9-1 to 9-8 to generate the transmission pulses, and a controller 5 controls the transmission trigger generator 10 and a transmission power source 11. The transmission power source 11 supplies the transmission pulse generators 9-1 to 9-8 with a voltage that determines an amplitude of the transmission pulses to be generated by the transmission pulse generators 9-1 to 9-8. An output side capacitor 7 is provided to stabilize a voltage of the transmission power source 11.

Reception amplifiers 12-1 to 12-8 appropriately amplify signals from the transducers 8-1 to 8-8, respectively, that have received a reflected ultrasonic wave. A beam former 13 subjects the amplified signals to delay addition, and a wave detector 14 detects the resulting signals. A scan converter (DSC) 15 subjects the detected signals to scan conversion, and a display 16 displays an image based on the resulting signals.

Recently, a single ultrasonic diagnostic apparatus can accommodate a Doppler mode in which blood flow information is displayed according to a spectrum, a color flow mode in which blood blow information is displayed in colors, as well as a B-mode in which an image is displayed by converting amplitude information into luminance, so as to perform a different mode operation for each scan.

As compared with the B-mode that requires a high resolution, the color flow mode and the Doppler mode require a high sensitivity. Accordingly, for a diagnosis, the wave number of a transmission waveform per pulse in the B-mode often is set lower than that in the color flow mode or the Doppler mode.

There are regulations on the intensity of an ultrasonic wave that can be incident on the inside of the body. In the case of a high wave number, the power per unit time becomes higher even with the same amplitude, and accordingly the amplitude needs to be set lower. On the other hand, in the B-mode in which the wave number is low, the amplitude needs to be increased within a stipulated range so as to increase a S/N ratio.

Consequently, in order to switch mutually between the B-mode, the color flow mode, and the Doppler mode at a high speed, it is necessary to change the output voltage of the transmission power source 11 rapidly. However, in the method as shown in FIG. 4 in which the single transmission power source 11 supplies power to all the transmission pulse generators 9-1 to 9-8, high-speed switching is difficult due to the large amount of power supply.

To solve this problem, for example, Patent Document 1 describes a method in which a plurality of power sources are provided and a power source to supply power is selected by a switch.

Figure 5A:
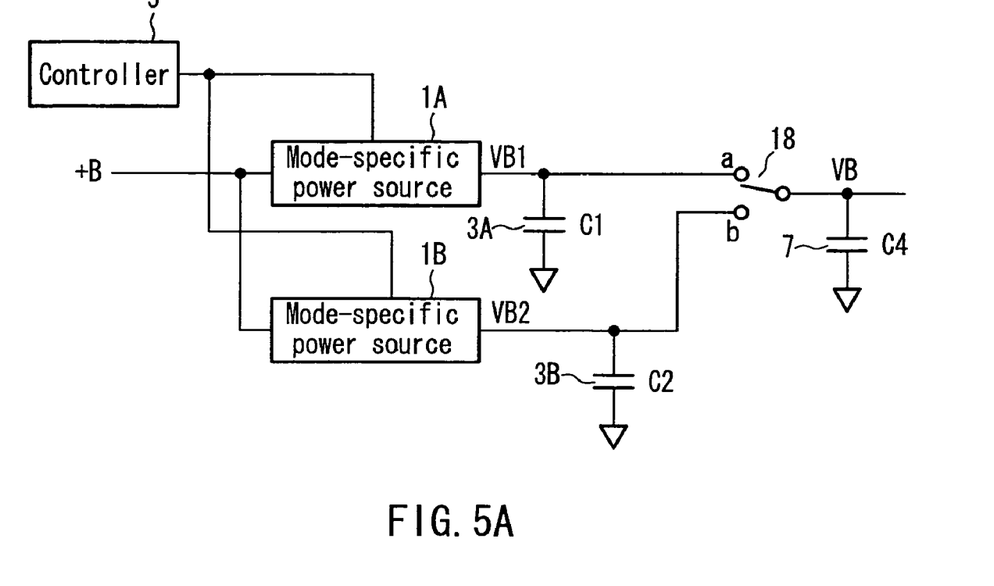
FIG. 5A is a block diagram of a transmission power source unit constituting the conventional ultrasonic diagnostic apparatus.
Figure 5B:
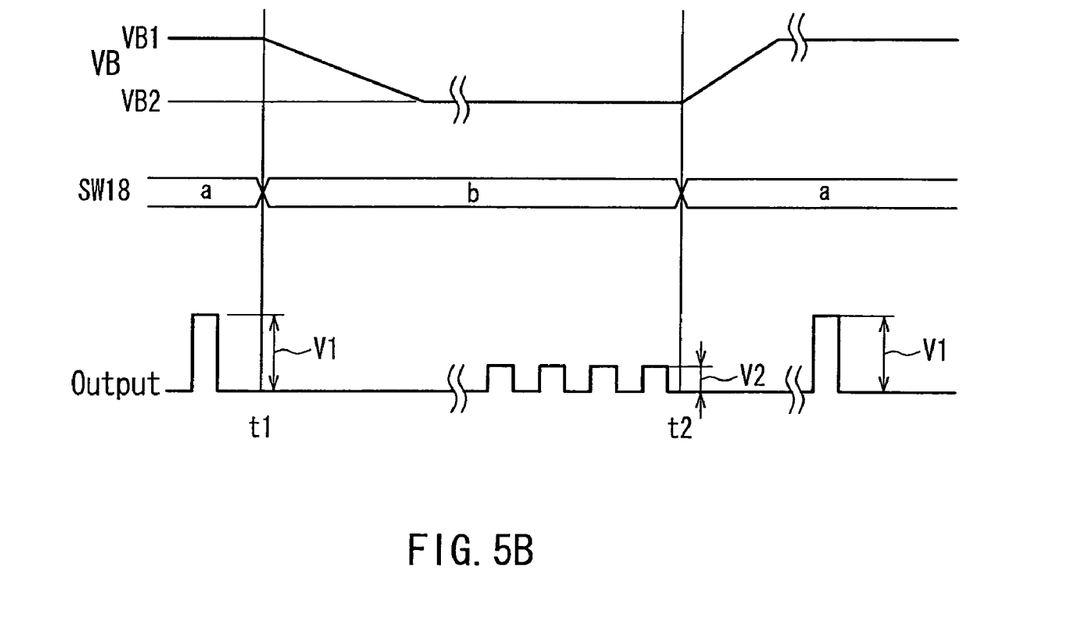
FIG. 5B is a timing chart showing an operation of the ultrasonic diagnostic apparatus in FIG. 5A in a compound mode.

FIG. 5A is a block diagram showing a configuration from a transmission power source to transmission pulse generators (not shown) in the ultrasonic diagnostic apparatus described in Patent Document 1. FIG. 5B is a timing chart showing switching of a transmission voltage. This ultrasonic diagnostic apparatus includes mode-specific power sources 1A and 1B for supplying power, a controller 5 for controlling the voltage of the mode-specific power sources 1A and 1B, power source side capacitors 3A and 3B for stabilizing the voltage of the mode-specific power sources 1A and 1B, respectively, a mode changeover switch 18 for switching between the mode-specific power sources 1A and 1B, and an output side capacitor 7. When generating transmission pulses, the transmission pulse generators rapidly consume power, followed by a voltage drop due to an internal resistance of the mode changeover switch 18 not being zero, and the output voltage decreases. The output side capacitor 7 is used as a temporary power source in such a case.

In FIG. 5B, VB represents an output voltage VB shown in FIG. 5A to be supplied to the transmission pulse generators. SW18 represents a connection state of the mode changeover switch 18. Output represents a voltage of transmission pulses for driving a transducer transmitted from the transmission pulse generators. When a transmission waveform with an amplitude V1 is generated to be transmitted to the transducer as Output for the B-mode (before Time t1), the mode changeover switch 18 is connected to an a side, so that a voltage VB1 is supplied from the mode-specific power source 1A. Then, when a transmission waveform with an amplitude V2 lower than the amplitude V1 is generated for the color flow mode (after Time t1), the mode changeover switch 18 is connected to a b side, so that an output voltage VB2 of the mode-specific power source 1B is supplied, and VB becomes equal to VB2. By repeating this operation, transmission and reception for the B-mode and those for the color flow mode are performed in a time-sharing manner.

Patent Document 1: JP 11(1999)-290321 A

DISCLOSURE OF INVENTION

Problem to be Solved by the Invention

In the case of supplying power by switching between the plurality of mode-specific power sources with the switch as shown in FIG. 5B, when the voltage VB1 is switched to the voltage VB2 lower than the voltage VB1, the output side capacitor 7 ineffectively consumes power to discard power stored therein, which leads to an increase in power consumption and heating value.

It is an object of the present invention to solve the above-mentioned problems and to provide an ultrasonic diagnostic apparatus that reuses power stored in the output side capacitor to reduce power consumption.

Means for Solving Problem

An ultrasonic diagnostic apparatus according to the present invention includes: a plurality of transducers for transmitting and receiving an ultrasonic wave; transmission pulse generators for generating pulses that allow the transducers to transmit the ultrasonic wave; a transmission power source for supplying power to the transmission pulse generators; and an output side capacitor for stabilizing a voltage of the transmission power source. The transmission power source includes: a plurality of mode-specific power sources for outputting a voltage corresponding to each of a plurality of signal processing modes; a power source side capacitor connected to an output side of each of the mode-specific power sources for stabilizing the voltage; and a mode changeover switch provided between the output side of the mode-specific power sources and the output side capacitor for switching between the mode-specific power sources that supply power to the transmission pulse generators. In this ultrasonic diagnostic apparatus, the transmission power source further includes: a power supplying power source connected to an input side of the mode-specific power sources for supplying power; and a power regeneration capacitor with a larger capacity than that of the output side capacitor, one electrode terminal of which is connected to a connection point between the power supplying power source and the input side of the mode-specific power sources and the mode changeover switch, and the other electrode terminal of which is connected to ground, and the mode changeover switch is capable of connecting the power regeneration capacitor, instead of the output side of each of the mode-specific power sources, to the output side capacitor. With this configuration, power charged in the output side capacitor can be returned to the input side of the mode-specific power sources, resulting in a reduction in power consumption.

Further, it is also possible that a plurality of power regeneration capacitors are included, and that the power regeneration switch is provided that is constituted to achieve a state in which the plurality of power regeneration capacitors are connected in cascade with respect to each of the mode-specific power sources and a state in which the plurality of power regeneration capacitors are connected in parallel with respect to the mode changeover switch.

Further, it is also possible that when the mode changeover switch connects the output side capacitor to the output side of each of the mode-specific power sources, the power regeneration switch is controlled to connect the plurality of power regeneration capacitors in cascade with respect to each of the mode-specific power sources and the power source side capacitor.

Further, it is also possible that when the mode changeover switch connects the output side capacitor to the plurality of power regeneration capacitors, the power regeneration switch is controlled to connect the plurality of power regeneration capacitors in parallel with respect to the mode changeover switch.

Further, it is also possible that a photo MOS relay is used as the mode changeover switch. With this configuration, by the use of a photo MOS relay as the switch, it is possible to reduce an internal resistance of the switch and to set a capacity of the capacitor between each of the mode-specific power sources and the transmission pulse generator to be low, resulting in a reduction in power consumption.

Further, it is also possible that a MEMS relay is used as the mode changeover switch. With this configuration, by the use of a MEMS relay as the switch, it is possible to reduce an internal resistance of the switch and to set a capacity of the capacitor between each of the mode-specific power sources and the transmission pulse generator to be low, resulting in a reduction in power consumption.

Further, it is also possible that a DC-DC converter is used as the transmission power source. With this configuration, by the use of a DC-DC converter as the step-up or step-down mode-specific power source, it is possible to perform efficient voltage conversion, and power consumed by voltage conversion can be reduced.

Effects of the Invention

An ultrasonic diagnostic apparatus according to the present invention transfers power stored in an output side capacitor to a power regeneration capacitor connected to a power source with a lower voltage when switching between a B-mode and a color mode or a Doppler mode in power supply to a transmission pulse generator, so as to reuse the power, whereby it is possible to reduce power consumption.

EXPLANATION OF LETTERS OR NUMERALS 1A, 1B, 1C, 1D Mode-specific power source
2 Power supplying power source
3A, 3B Power source side capacitor
4, 4A, 4B, 4C, 4D Power regeneration capacitor
5 Controller
6, 18 Mode changeover switch
7 Output side capacitor
8-1 to 8-8 Transducer
9-1 to 9-8 Transmission pulse generator
10 Transmission trigger generator
11 Transmission power source
12-1 to 12-8 Reception amplifier
13 Beam former
14 Wave detector
15 Scan converter (DSC)
16 Display
17A, 17B, 17C, 17D, 17E, 17F Power regeneration switch

DESCRIPTION OF THE INVENTION

Hereinafter, an embodiment of the present invention will be described with reference to FIG. 1.

First Embodiment

Figure 1A:
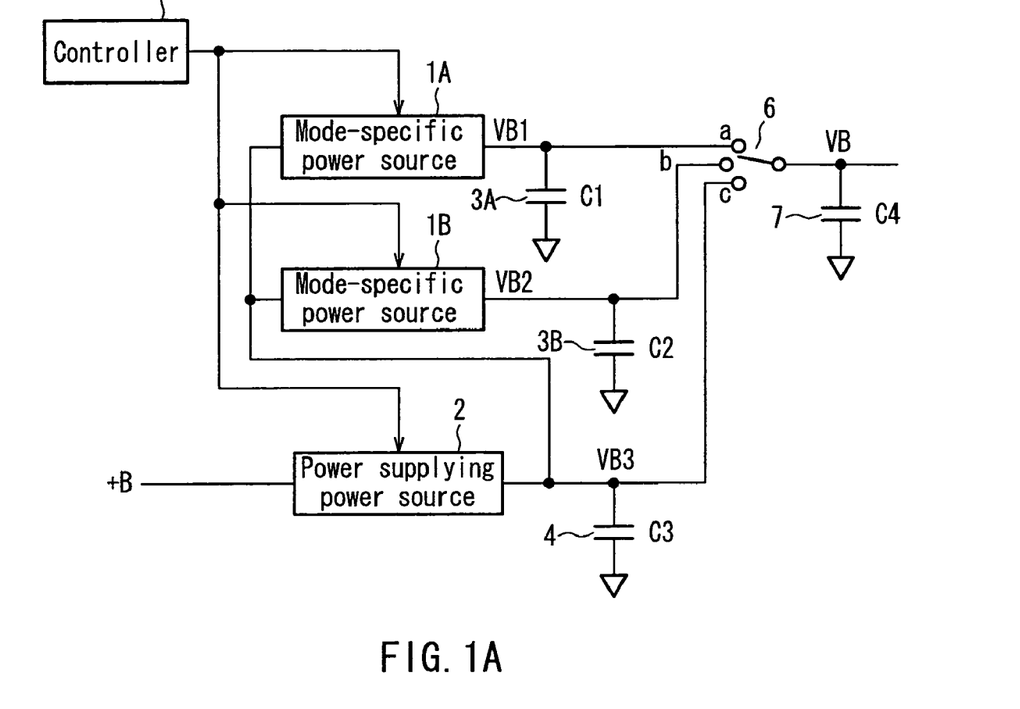
FIG. 1A is a block diagram of a transmission power source unit constituting an ultrasonic diagnostic apparatus according to a first embodiment of the present invention.
Figure 1B:
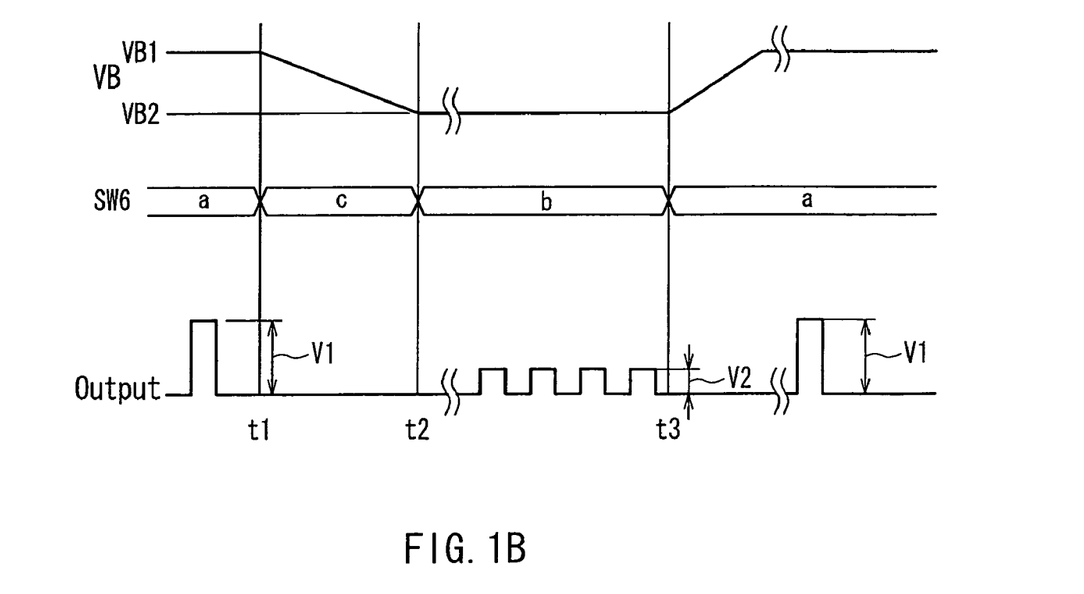
FIG. 1B is a timing chart showing an operation of the ultrasonic diagnostic apparatus in FIG. 1A in a compound mode.

FIG. 1A is a diagram showing a configuration of a transmission power source 11 (see FIG. 4) for supplying power to transmission pulse generators 9-1 to 9-8 (see FIG. 4) in a transmission unit for sector scanning in a first embodiment of the present invention. The transmission power source 11 includes mode-specific power sources 1A and 1B for supplying power to the transmission pulse generators 9-1 to 9-8, a power supplying power source 2 for supplying power to the mode-specific power sources 1A and 1B, power source side capacitors 3A and 3B for stabilizing a voltage of the mode-specific power sources 1A and 1B, respectively, and a power regeneration capacitor 4 for regenerating power. Each of the mode-specific power sources 1A and 1B generates a voltage corresponding to a signal processing mode (e.g., a B-mode or a color flow mode) of the ultrasonic diagnostic apparatus. Further, a mode changeover switch 6 is provided for connecting the transmission pulse generators 9-1 to 9-8 to either one of the mode-specific power sources 1A and 1B and the power supplying power source 2.

Further, a controller 5 controls the voltage of the mode-specific power sources 1A and 1B. An output side capacitor 7 is provided on the transmission-pulse-generators-9-1-to-9-8 side of the mode changeover switch 6 for stabilizing a voltage to the transmission pulse generators 9-1 to 9-8.

Herein, output voltages VB1, VB2, and VB3 of the mode-specific power sources 1A and 1B and the power supplying power source 2, respectively, satisfy the following relationship: VB1>VB2>VB3. Following the turning-on of the power to the ultrasonic diagnostic apparatus, the voltages of the mode-specific power sources 1A and 1B and the power supplying power source 2 are set under the control of the controller 5.

Next, with reference to FIG. 1B, a description will be given of an operation of switching between B-mode scanning and color flow mode scanning in a fine time-sharing manner, e.g., for each scanning line. In the description below, it is assumed that the mode-specific power source 1A is used for the B-mode and the mode-specific power source 1B is used for the color flow mode. In FIG. 1B, VB represents an electric potential at a position VB in FIG. 1A, i.e., the output voltage to the transmission pulse generators 9-1 to 9-8 (the voltage of the output side capacitor 7), SW6 represents a connection state of the mode changeover switch 6, and Output represents a voltage of transmission pulses for driving a transducer transmitted from the transmission pulse generators 9-1 to 9-8.

During the B-mode scanning (before Time t1), the mode changeover switch 6 is connected to a terminal a, so that power stored in the mode-specific power source 1A, the power source side capacitor 3A, and the output side capacitor 7 is supplied to the transmission pulse generators 9-1 to 9-8, and the transmission pulse generators 9-1 to 9-8 output transmission pulses with an amplitude V1.

After the transmission pulses for the B-mode are output (Time t1), the mode changeover switch 6 is shifted to a terminal c, so that the power stored in the output side capacitor 7 is transferred to the power regeneration capacitor 4 via the mode changeover switch 6. A capacity C3 of the power regeneration capacitor 4 and a capacity C4 of the output side capacitor 7 satisfies the following relationship: C3>C4. Accordingly, even when the voltage of the output side capacitor 7 decreases considerably, the voltage of the power regeneration capacitor 4 does not change significantly.

When the voltage VB of the output side capacitor 7 decreases to the voltage VB2 (Time t2), the mode changeover switch 6 is shifted to a terminal b. As a result, the voltage VB of the output side capacitor 7 becomes equal to VB2, and the transmission pulse generators generate transmission pulses with an amplitude V2 for the color flow mode.

Herein, each of the mode-specific power sources 1A and 1B includes a step-up circuit, so that the output voltage can be set higher than an input voltage. Therefore, it is possible to generate the voltages VB1 and VB2 from the voltage VB3 lower than VB1 and VB2. In terms of efficiency, it is preferable to use a switching system DC-DC converter as the step-up circuit included in the mode-specific power sources 1A and 1B.

After the transmission pulse generators 9-1 to 9-8 generate the transmission pulses for the color flow mode (Time t3), the mode changeover switch 6 is shifted again to the terminal a, and the output side capacitor 7 is charged. Then, the voltage VB becomes VB1, and the transmission pulse generators 9-1 to 9-8 generate the transmission pulses for the B-mode.

In the present embodiment, the power of the output side capacitor 7 stored during the B-mode is transferred to the power regeneration capacitor 4 connected to the power supplying power source 2 with a lower voltage, and is reused as power for the B-mode and the color mode by using the step-up circuit. Therefore, it is possible to suppress power consumption during switching between the modes.

As the mode changeover switch 6, a photo MOS relay or a relay using MEMS (Micro Electro Mechanical Systems) may be used to perform high-speed switching with a low internal resistance.

Second Embodiment

Figure 2A:
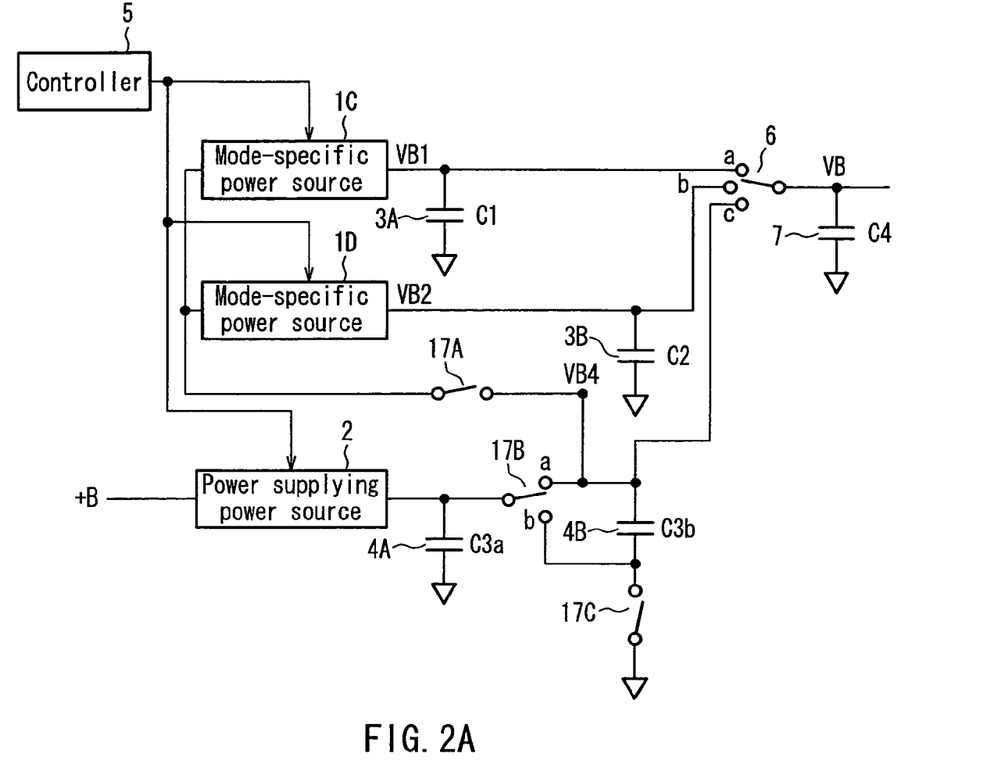
FIG. 2A is a block diagram of a transmission power source unit constituting an ultrasonic diagnostic apparatus according to a second embodiment of the present invention.

FIG. 2A is a block diagram showing a transmission power source 11 (see FIG. 4) in a transmission unit for sector scanning in a second embodiment of the present invention. The present embodiment is different from the first embodiment (see FIG. 1) in that the power regeneration capacitor 4 is replaced by two power regeneration capacitors 4A and 4B and that power regeneration switches 17A, 17B, and 17C for connecting the mode changeover switch 6, mode-specific power sources 1C and 1D, and the power supplying power source 2 are provided additionally. Further, the mode-specific power sources 1C and 1D adopt a step-down system instead of a step-up system. In FIG. 2A, VB4 represents a voltage between the power regeneration switch 17A and the power regeneration capacitor 4B.

Figure 2B:
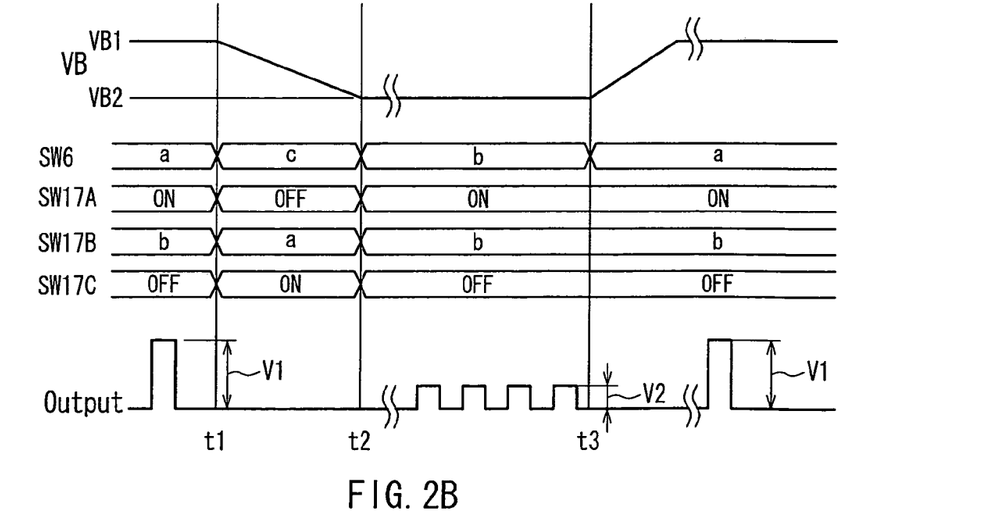
FIG. 2B is a timing chart showing an operation of the ultrasonic diagnostic apparatus in FIG. 2A in a compound mode.

FIG. 2B is a timing chart showing the generation of a transmission pulse and switching timings of the power regeneration switches 17A, 17B, and 17C. In the figure, SW6, SW17A, SW17B, and SW17C represent connection states of the mode changeover switch 6, the power regeneration switches 17A, 17B, and 17C, respectively.

During B-mode scanning (before Time t1), the mode changeover switch 6 is connected to a terminal a, the power regeneration switch 17A is turned ON, the power regeneration switch 17B is connected to a terminal b, and the power regeneration switch 17C is turned OFF. Accordingly, the power regeneration capacitors 4A and 4B are connected in cascade with respect to the mode-specific power source 1C, and VB4 becomes the sum of voltages between terminals of the capacitors, which is input to the mode-specific power sources 1C and 1D.

After transmission pulses for the B-mode are output (Time t1), the mode changeover switch 6 is shifted to a terminal c (power regeneration terminal), the power regeneration switch 17A is turned OFF, the power regeneration switch 17B is shifted to a terminal a, and the switch 17C is turned ON. Accordingly, the two power regeneration capacitors 4A and 4B are connected in parallel with respect to the mode changeover switch 6, and the voltage VB4 applied to the power regeneration capacitors 4A and 4B becomes lower than the voltage VB of the output side capacitor 7. The electric charge of the output side capacitor 7 is transferred to the power regeneration capacitors 4A and 4B, and the voltage of the output side capacitor 7 decreases to VB2.

When the voltage of the output side capacitor 7 decreases to VB2 (Time t2), the mode changeover switch 6 is shifted to a terminal b, the power regeneration switch 17A is turned ON, the power regeneration switch 17B is shifted to the terminal b, and the power regeneration switch 17C is turned OFF. At this time, the power regeneration capacitors 4A and 4B are connected in cascade with respect to the mode-specific power source 1D, and a voltage higher than VB2 is applied to the mode-specific power source. The mode-specific power source 1D that outputs the voltage VB2 is connected to the output side capacitor 7 to supply power of the voltage VB2 to the transmission pulse generators 9-1 to 9-8.

At Time t3, the mode changeover switch 6 is connected to the terminal a, so that the voltage VB increases to the voltage VB1.

As described above, the ultrasonic diagnostic apparatus of the present embodiment includes the output side capacitor 7 and the power regeneration capacitors 4A and 4B, and switches connections with the mode changeover switch 6, 17A, 17B, and 17C so as to set the voltage of the output side capacitor 7 and to return the power discarded by the output side capacitor 7 to the mode-specific power sources 1C and 1D. Therefore, the ultrasonic diagnostic apparatus can suppress power consumption.

In the present embodiment, although two power regeneration capacitors are provided, three or more power regeneration capacitors may be provided.

Figure 3A:
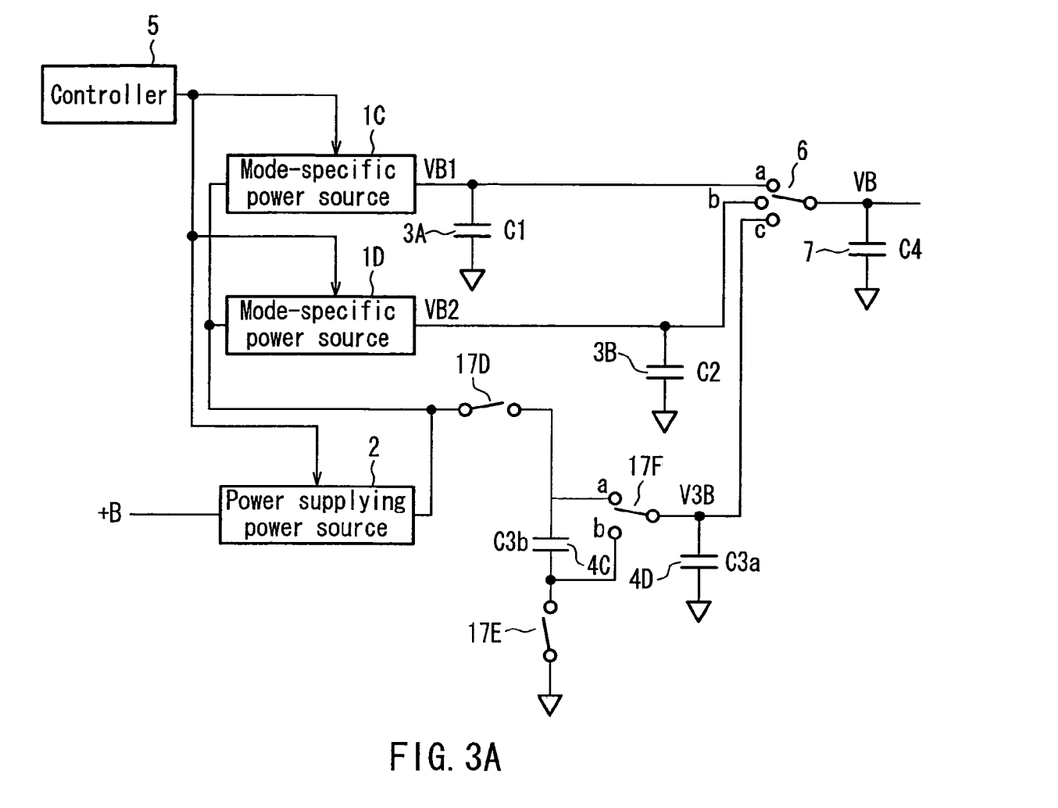
FIG. 3A is a block diagram of a transmission power source unit constituting another ultrasonic diagnostic apparatus according to the second embodiment of the present invention.

Further, as shown in FIG. 3A, it is also possible that the mode-specific power sources 1C and 1D are connected directly to the power supplying power source 2 and that two power regeneration capacitors 4C and 4D as well as three power regeneration switches 17D, 17E, and 17F are provided. The power regeneration switch 17D connects the power regeneration capacitors 4C and 4D to the mode-specific power sources 1C and 1D, and the power regeneration switch 17E determines whether or not one terminal of the power regeneration capacitor 4C is connected to ground. The power regeneration switch 17F connects the power regeneration capacitor 4D to either one of the terminals of the power regeneration capacitor 4C.

Figure 3B:
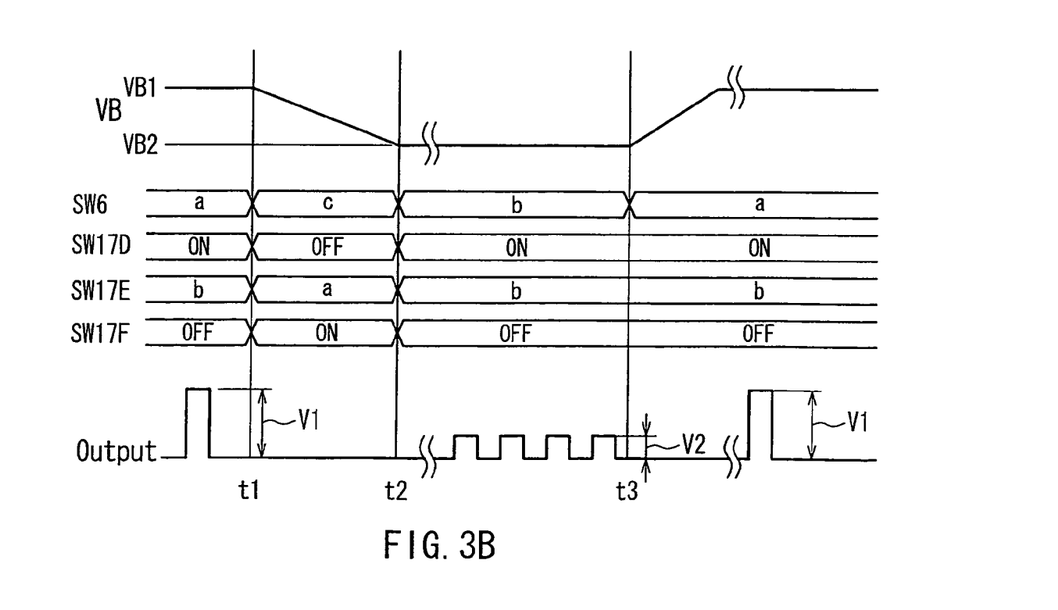
FIG. 3B is a timing chart showing an operation of the ultrasonic diagnostic apparatus in FIG. 3A in a compound mode.

FIG. 3B is a timing chart showing the generation of a transmission pulse and switching timings of the power regeneration switches 17D, 17E, and 17F. In the figure, SW (switch) 17D, 17E, and 17F replace SW 17A, 17B, and 17C, respectively, in the timing chart in FIG. 2B.

With this configuration, it is also possible to reduce power consumption.

INDUSTRIAL APPLICABILITY

The present invention is applied usefully to an ultrasonic diagnostic apparatus that accommodates a plurality of signal processing modes and reuses power stored in the output side capacitor so as to reduce power consumption and heating value.

The invention claimed is:

1. An ultrasonic diagnostic apparatus comprising: a plurality of transducers for transmitting and receiving an ultrasonic wave; transmission pulse generators for generating pulses that allow the transducers to transmit the ultrasonic wave; a transmission power source for supplying power to the transmission pulse generators; and an output side capacitor for stabilizing a voltage of the transmission power source, the transmission power source including: a plurality of mode-specific step-up power sources for outputting a voltage corresponding to each of a plurality of signal processing modes; a power source side capacitor connected to an output side of each of the mode-specific step-up power sources for stabilizing the voltage; and a mode changeover switch provided between the output side of the mode-specific step-up power sources and the output side capacitor for switching between the mode-specific step-up power sources that supply power to the transmission pulse generators, wherein the transmission power source further includes:

a power supplying power source connected to an input side of the mode-specific step-up power sources for supplying power; and a power regeneration capacitor with a larger capacity than that of the output side capacitor, one electrode terminal of which is connected to a connection point between the power supplying power source and the input side of the mode-specific step-up power sources and the mode changeover switch, and the other electrode terminal of which is connected to ground, and the mode changeover switch is capable of connecting the power regeneration capacitor, instead of the output side of each of the mode-specific step-up power sources, to the output side capacitor.

2. The ultrasonic diagnostic apparatus according to claim 1, wherein a photo MOS relay is used as the mode changeover switch.

3. The ultrasonic diagnostic apparatus according to claim 1, wherein a MEMS (Micro Electro Mechanical Systems) relay is used as the mode changeover switch.

4. The ultrasonic diagnostic apparatus according to claim 1, wherein a DC-DC converter is used as the transmission power source.

5. An ultrasonic diagnostic apparatus comprising a plurality of transducers for transmitting and receiving an ultrasonic wave; transmission pulse generators for generating pulses that allow the transducers to transmit the ultrasonic wave; a transmission power source for supplying power to the transmission pulse generators; and an output side capacitor for stabilizing a voltage of the transmission power source, the transmission power source including: a plurality of mode-specific step-down power sources for outputting a voltage corresponding to each of a plurality of signal processing modes; a power source side capacitor connected to an output side of each of the mode-specific step-down power sources for stabilizing the voltage; and a mode changeover switch provided between the output side of the mode-specific step-down power sources and the output side capacitor for switching between the mode-specific step-down power sources that supply power to the transmission pulse generators, wherein the transmission power source further includes:

a power supplying power source connected to an input side of the mode-specific step-down power sources for supplying power;

a power regeneration capacitor, including a plurality of capacitors, with a larger capacity than that of the output side capacitor, one electrode terminal of which is connected to a connection point between the power supplying power source and the input side of the mode-specific step-down power sources and the mode changeover switch, and the other electrode terminal of which is connected to ground; and a power regeneration switch for switching between a connection point between an output side of the power supplying power source and the power regeneration capacitor and the input side of the mode-specific step-down power sources; and the power regeneration switch is constituted to achieve a state in which the plurality of power regeneration capacitors are connected in cascade with respect to the input side of each of the mode-specific step-down power sources and a state in which the plurality of power regeneration capacitors are connected in parallel with respect to the mode changeover switch.

6. The ultrasonic diagnostic apparatus according to claim 5, wherein when the mode changeover switch connects the output side capacitor to the output side of each of the mode-specific power sources, the power regeneration switch is controlled to connect the plurality of power regeneration capacitors in cascade with respect to each of the mode-specific power sources and the power source side capacitor.

7. The ultrasonic diagnostic apparatus according to claim 6, wherein when the mode changeover switch connects the output side capacitor to the plurality of power regeneration capacitors, the power regeneration switch is controlled to connect the plurality of power regeneration capacitors in cascade with respect to the mode changeover switch.

8. The ultrasonic diagnostic apparatus according to claim 5, wherein when the mode changeover switch connects the output side capacitor to the plurality of power regeneration capacitors, the power regeneration switch is controlled to connect the plurality of power regeneration capacitors in parallel with respect to the mode changeover switch.

\* \* \* \* \*